United States Patent [19]

Corbin et al.

[11] Patent Number: 4,918,237

[45] Date of Patent: Apr. 17, 1990

[54] PROCESS FOR THE MANUFACTURE OF 1,4-BIS(4-PHENOXYBENZOYL)BENZENE WITH CERTAIN METAL-CONTAINING CATALYSTS

[75] Inventors: David R. Corbin, West Chester, Pa.; Enio Kumpinsky, Wilmington, Del.

[73] Assignee: E. I. du Pont de Nemours and Company, Wilmington, Del.

[21] Appl. No.: 322,622

[22] Filed: Mar. 13, 1989

[51] Int. Cl.⁴ .................................. C07C 45/46
[52] U.S. Cl. ....................................... 568/322
[58] Field of Search ............................. 568/322

[56] References Cited

U.S. PATENT DOCUMENTS

| | | | |
|---|---|---|---|
| 2,879,296 | 3/1959 | Prile | 568/323 |
| 3,288,855 | 11/1968 | Schisla et al. | 568/322 |
| 3,360,566 | 12/1967 | Linder et al. | 568/323 |
| 4,827,041 | 5/1989 | Ford et al. | 568/322 |

FOREIGN PATENT DOCUMENTS

| | | | |
|---|---|---|---|
| WO86/07598 | 12/1986 | PCT Int'l Appl. | 568/322 |
| 1086021 | 10/1967 | United Kingdom | 568/322 |
| 2172294A | 3/1986 | United Kingdom | 568/322 |

OTHER PUBLICATIONS

Ustinov et al., Chem. Abst., vol. 90, #87049c, (1979).
Buehler, Synthesis, pp. 533–542, (1972).

*Primary Examiner*—James H. Reamer
*Attorney, Agent, or Firm*—Paul R. Steyermark

[57] ABSTRACT

1,4-Bis(4-phenoxybenzoyl)benzene is made in a homogeneous or heterogeneous system by a reaction of diphenyl ether with 1,4-benzenedicarbonyl chloride at 220°–258° C. in the presence of certain iron, gallium, and indium compounds in catalytic amounts. The mole ratio of diphenyl ether to 1,4-dicarbonyl chloride is 5:1 to 25:1 and the mole ratio of 1,4-benzenedicarbonyl chloride to the catalyst is 1000:1 to 10:1.

10 Claims, No Drawings

PROCESS FOR THE MANUFACTURE OF 1,4-BIS(4-PHENOXYBENZOYL)BENZENE WITH CERTAIN METAL-CONTAINING CATALYSTS

BACKGROUND OF THE INVENTION

This invention relates to a process for the manufacture of 1,4-bis(4-phenoxybenzoyl)benzene in a homogeneous or heterogeneous system, in the presence of certain metal salt catalysts.

1,4-Bis(4-phenoxybenzoyl)benzene (sometimes referred to hereinafter as BPBB) which is an important intermediate in the manufacture of polyetherketone resins, is currently made industrially by a reaction of 1,4-benzenedicarbonyl chloride with diphenyl ether in the presence of a Friedel-Crafts catalyst, usually aluminum chloride, which is employed in an amount of at least three moles per mole of 1,4-benzenedicarbonyl chloride. Polyetherketones are a well known generic class of commercial resins, which include polyetherketones proper, poly(ether ether ketones), poly(ether ketone ketones), and mixed copolymers having segments of both the first named type and the last named type. Diphenyl ether normally is used in a significant excess to minimize formation of higher oligomers. Normally, the reaction is carried out in a solvent such as, e.g., 1,2-dichlorobenzene, at a temperature of approximately 0° C. After the reaction is complete, methanol is added to precipitate the product and remove the catalyst therefrom. The product is filtered off, washed repeatedly with methanol, and recrystallized from N,N-dimethylacetamide or 1,2-dichlorobenzene.

The use of aluminum chloride presents various shortcomings. The recovered aluminum chloride cannot be reused and this creates a waste disposal problem as well as adds to the cost of the operation. Further, aluminum chloride does not have a high para,para-isomer selectivity, so that it tends to also produce a fair proportion of the ortho,para-isomer, i.e., [1-(2-phenoxy),4-(4-phenoxy)]dibenzoylbenzene. Because of extensive purification, requiring repeated filtrations, long recovery times are needed.

BPBB can also be manufactured by a reaction of 1,4-benzenedicarbonyl chloride with excess diphenyl ether at 190°–258° C. in the presence of hydrogen-exchanged zeolite catalysts, which are highly para,para-isomer selective, as taught in the copending application of Corbin et al., Ser. No. 07/218941, filed July 14, 1988, and now allowed. While the invention disclosed and claimed in that allowed application represents a considerable advantage over the above-described current industrial process, it too has certain drawbacks. It requires a very large excess of diphenyl ether as well as a significant amount of zeolite catalyst. The high ratio of diphenyl ether to 1,4-benzenedicarbonyl chloride and the large amount of catalyst make the operation quite costly. Further, the hydrogen-exchanged zeolite must be either regenerated or disposed of, which again increases the manufacturing cost.

It is, therefore, desirable to be able to produce BPBB in an isomer-selective, simple operation, requiring no solvent, run with a smaller excess of diphenyl ether, and with a significantly smaller amount of catalyst. It further would be highly desirable to be able either to reuse the catalyst without regeneration or to dispose of it without major expense.

SUMMARY OF THE INVENTION

According to this invention, there is now provided a process for the manufacture of BPBB, said process comprising contacting diphenyl ether for a period of about 60 to about 360 minutes, at a temperature of about 220°–258° C., with 1,4-benzenedicarbonyl chloride in respective mole ratios of about 5:1 to about 25:1 in the presence of at least one catalyst selected from the group consisting of unsupported iron (II) chloride (ferrous chloride), iron (II) sulfate (ferrous sulfate), gallium (II) sulfate, and indium (III) sulfate; and iron (II) chloride, iron (II) sulfate, gallium (III) sulfate, indium (III) sulfate, and iron (III) chloride (ferric chloride) on an inert support; and the mole ratio of 1,4-benzenedicarbonyl chloride to the catalyst being about 10:1 to 1000:1, and recovering the BPBB product by separating it from both excess diphenyl ether and the catalyst.

DETAILED DESCRIPTION OF THE INVENTION

The basic reaction involved in the process of this invention is shown in the following equation:

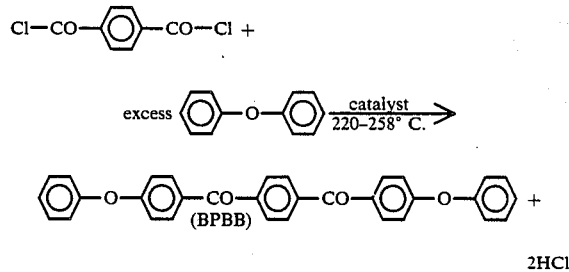

The starting materials for this reaction are well known and readily available.

1,4-Benzenedicarbonyl chloride, also known as terephthalyl chloride, can be made from terephthalic acid by any suitable known reaction, e.g., with phosphorus pentachloride, phosphorus trichloride, or thionyl chloride.

1,4-Benzenedicarbonyl chloride also is commercially available, i.a., from E. I. Du Pont de Nemours and Company.

Diphenyl ether is commercially available, i.a., from Dow Chemical Company.

The catalysts are available from several sources, including Alfa Division of Morton Thiokol Co. and Aldrich Chemicals. They can be used in a homogenous system since they dissolve to a sufficient extent in the reaction mixture at the reaction temperature, or in a heterogenous system when deposited on an inert support material. Suitable support materials include, for example, silica, alumina, and carbon.

In the practical operation of the process of this invention, the reactants and the catalyst are charged into a reactor, and the temperature is raised to 220° to 258° C. While excess diphenyl ether is necessary, it is preferred to keep the mole ratio of diphenyl ether to 1,4-benzenedicarbonyl chloride within the range of 6–10:1. The preferred mole ratio of 1,4-benzenedicarbonyl chloride to catalyst is 50 to 300. The preferred reaction temperature range is 240°–258° C. Within this temperature range, the preferred reaction time is 180 to 360 min. The most preferred time and temperature conditions are about 5 hours at 250° C. The most preferred mole ratio of diphenyl ether to 1,4-benzenedicarbonyl chloride is about 8, and the most preferred mole ratio of 1,4-benzenedicarbonyl chloride to catalyst is about 200. The preferred unsupported catalyst is ferrous chloride.

While many metal compounds have been found to catalyze the condensation of diphenyl ether with 1,4-benzenedicarbonyl chloride, only BPBB made in the presence of those catalysts listed in the Summary of the Invention gave a polyetherketone which was thermally stable.

Generally, if the process temperature is too low, the starting materials will be converted predominantly to adducts of one mole of diphenyl ether with one mole of 1,4-benzenedicarbonyl chloride; conversion to the desired product, BPBB, will be minimal. If the temperature is too high (if the reaction is run under pressure), conversion may also be reduced because of large amounts of byproducts and degradation of 1,4-benzenedicarbonyl chloride. If the mole ratio of diphenyl ether to 1,4-benzenedicarbonyl chloride is too low, the conversion of BPBB will be low; if it is too high, the benefit of having a high BPBB product concentration in the reaction mixture will not be realized. If the mole ratio of 1,4-benzenedicarbonyl chloride to catalyst is too high the reaction is too slow; if it is too low, the separation of BPBB from the catalyst may be more difficult.

When the catalyst is in solution, in a homogenous system, it is not recovered but is discarded; however, a supported catalyst, used in a heterogeneous system, can be recovered and reused without need for regeneration. When the catalyst can be reused, an additional benefit is realized. The supported catalyst can be readily separated, by filtration or otherwise, from the hot liquid reaction mixture. The unsupported catalyst contaminating the solid BPBB product can be easily removed from by washing with a suitable solvent, such as, e.g., methanol.

BPBB, which crystallizes from the solution in diphenyl ether after cooling (for example, to 30°-50° C.), in any event must be washed with a solvent such as methanol to remove diphenyl ether and any adduct of one mole of diphenyl ether with one mole of 1,4-benzenedicarbonyl chloride that might have crystallized during the cooldown. Other solvents which are suitable for this purpose are, i.a., tetrahydrofuran, isopropyl alcohol, and acetone. BPBB can be further purified, if desired, by recrystallization from solvents such as, e.g., N,N-dimethylacetamide and 1,2-dichlorobenzene. The solvent-washed or the recrystallized BPBB can be used in the final step of the preparation of a polyetherketone by condensation with additional 1,4-benzenedicarbonyl chloride (or another dicarboxylic acid dichloride) in a manner known to the art.

Excess diphenyl ether recovered from the BPBB preparation according to the process of this invention can be reused several times without purification. When purification is deemed advisable, this is done most conveniently by distillation at a reduced pressure.

While the above description concerns a batch process of this invention, the process can be adapted to a continuous operation, where the critical variables to be controlled are the mole ratio of 1,4-benzenedicarbonyl chloride to catalyst, the mole ratio of diphenyl ether to 1,4-benzenedicarbonyl chloride, temperature, and residence time. Various routine operations can be modified in both batch process and the continuous process so as to obtain the greatest operational efficiency; e.g., separation of solids from liquids can be achieved not only by filtration but also by decantation or centrifugation, whichever is the most convenient, i.a., from the standpoint of time, energy requirement, and equipment availability.

This invention is now illustrated by representative examples of certain preferred embodiments thereof. In all the examples, the conversion of 1,4-benzenedicarbonyl chloride to BPBB was calculated as follows:

$$\text{conversion (\%)} = \frac{\text{moles of BPBB in the product}}{\text{moles of 1,4-benzenedicarbonyl chloride in the feed}} \times 100$$

Any partial reaction product, comprising one molecule of each reactant that may have been formed as a side product, was disregarded. All the catalysts were used as received.

EXAMPLE 1

Different metal compounds were used to catalyze BPBB synthesis. Diphenyl ether (134 g, 0.787 mole) was combined with 20 g (0.099 mole) of 1,4-benzenedicarbonyl chloride and 0.5 g of metal compound in a reactor. The mixture was heated to 250° C. under a nitrogen purge and held at this temperature for five hours. Diphenyl ether (187 g) at 80° C. was added to the reactor to quench the reaction to about 180° C. The solution was filtered at about 180° C. and was allowed to cool. The product was filtered at 50° C., washed with methanol and dried. The results of these exeriments are summarized in Table I, below. The following column designations are used:

A = metal compound
B = conversion to BPBB.
C = a/b melting peaks by differential scanning calorimetry, °C., with heating rate of 20° C./min in nitrogen atmosphere, where "a" and "b" are the melting peaks in the first heat and remelt, respectively; a minus sign means very impure material, with shoulders and/or secondary peaks. When the melt and remelt temperatures are only a few degrees apart, the material is reasonably thermally stable and thus usually reasonably pure, but this is not the only criterion of purity.
D = melt stability of polymer made from BPBB, where "+" = melt stable; "−" = melt unstable; "0" = not determined because of lack of purity or low yield.

TABLE I

| A | B | C | D |
|---|---|---|---|
| Aluminum chloride | 57.6 | 212/208 | 0 |
| Aluminum bromide (1 g used) | 49.3 | 210/206 | 0 |
| Aluminum sulfate octadecahydrate | nil | | |
| Bis(cyclopentadienyl) titanium dichloride | nil | | |
| Vanadium (V) oxide | 17.3 | 212/212 | 0 |
| Chromium (III) chloride hexahydrate | traces | | |
| Chromium (III) oxide | 13.8 | 212/212 | −0 |
| Manganese chloride tetrahydrate | nil | | |
| Iron metal powder (0.1 g used) | 70.6 | 212/204 | −0 |
| Iron (II) chloride tetrahydrate | 72.9 | 217/208 | + |
| Iron (III) chloride | 77.0 | 214/205 | − − |
| Iron (II) sulfate heptahydrate | 73.9 | 215/206 | + |
| Iron (III) sulfate | 73.9 | 210/202 | − − |

TABLE I-continued

| A | B | C | D |
|---|---|---|---|
| Iron (III) fluoride | 78.8 | 211/203 | — |
| Iron (III) nitrate nonahydrate | 72.3 | 211/204 | — |
| Iron (III) oxide (hematite) | 70.5 | 212/213 | −0 |
| Iron (II) sulfide | 75.3 | 213/204 | 0 |
| Cobalt chloride hexahydrate | 57.6 | 214/208 | −0 |
| Nickel (II) chloride hexahydrate | traces | | |
| Copper (I) chloride | 20.7 | 213/213 | 0 |
| Zinc chloride | 69.0 | 208/204 | −0 |
| Gallium (III) chloride | 83.7 | 213/207 | — |
| Gallium (III) sulfate | 74.6 | 211/204 | + |
| Zirconium (IV) chloride | 34.6 | 213/208 | 0 |
| Molybdenum (VI) oxide | 73.3 | 211/205 | 0 |
| Ruthenium chloride dihydrate | 12.3 | 219/217 | 0 |
| Rhodium chloride trihydrate | nil | | |
| Palladium (II) chloride | nil | | |
| Silver nitrate | nil | | |
| Cadmium nitrate tetrahydrate | nil | | |
| Indium (III) sulfate hydrate | 74.6 | 216/208 | + |
| Tin (II) sulfate | nil | | |
| Cerium (III) nitrate | 3.5 | 181/150 | −0 |
| Europium chloride | 19.6 | 206/203 | −0 |
| Tantalum (V) fluoride | 75.9 | 212/205 | — |
| Tungsten (VI) oxide | 63.0 | 211/203 | 0 |
| Rhenium (III) chloride | 76.6 | 216/108 | −0 |
| Platinum (1%) on alumina | 2.0 | 217/214 | 0 |
| Mercury (II) chloride | nil | | |
| Thallium (I) sulfate | nil | | |
| Lead (II) chloride | nil | | |
| Lead (II) titanate | nil | | |

EXAMPLE 2

Iron (III) chloride on silica catalyst, Alfa 10677 from Morton Thiokol, was tested in a repetitive experiment. The same catalyst was used in all the runs with no regeneration. Between the runs, the catalyst was stored in a vacuum oven at 110° C. under a nitrogen purge. This catalyst, 1.5 g, was combined with 267.5 g (1.572 mole) of diphenyl ether and 40 g (0.197 mole) of 1,4-benzenedicarbonyl chloride in each run. The mixture was heated under nitrogen to 250° C. and held at that temperature for five hours. Diphenyl ether, 374.5 g, at 80° C. was added to the reactor to quench the reaction to about 180° C. The solution was filtered at about 180° C. and allowed to cool; crystals of BPBB began precipitating at about 140° C. The product was filtered at 50° C., washed with methanol and dried. The conversions to BPBB are given below.

TABLE II

| Run Number | Amount of BPBB (g) | Conversion (%) |
|---|---|---|
| 1 | 72.3 | 78.0 |
| 2 | 66.1 | 71.3 |
| 3 | 72.5 | 78.2 |
| 4 | 73.1 | 78.9 |

This example shows that a supported iron (III) catalyst can be reused several times without regeneration, retaining its catalytic activity.

EXAMPLE 3

Diphenyl ether recovered from the first run of Example 1 was reused without purification, except that it was refiltered at 30° C. one day after that run. This recovered diphenyl ether, (134 g, 0.787 mole) was combined with 20 g (0.099 mole) of 1,4-benzenedicarbonyl chloride and 0.75 g of fresh, supported iron (III) chloride on silica catalyst (Alfa 10677 from Morton Thiokol) in a reactor. The mixture was heated in the reactor to 250° C. under a nitrogen purge and held at 250° C. for five hours. Recovered diphenyl ether, 187 g, at 80° C. was added to quench the reaction to about 180°. The solution was filtered at about 180° C. and allowed to cool; the crystals of BPBB began precipitating at about 140° C. The product was filtered at 50° C., washed with methanol, and dried. It weighed 33.10 g, for a conversion of 71.4%. Very small amounts of impurities were found by differential scanning calorimetry. This example shows that diphenyl ether can be reused without redistillation.

EXAMPLE 4

This example illustrates four different BPBB purification procedures. Iron (III) chloride on silica catalyst, Alfa 10677 of Morton Thiokol, was dried overnight in a vacuum oven at 110° C. under nitrogen purge. Three grams of this catalyst was combined with 535 g (3.143 moles) of diphenyl ether and 80 g (0.394 mole) of 1,4-benzenedicarbonyl chloride in a reactor. The mixture was heated to 50° C. and kept at this temperature for 30 minutes under intense nitrogen purge to eliminate any residual oxygen from the system. The mixture was then heated under low nitrogen purge to 250° C. and held at that temperature for five hours. A total of 749 g (4.401 mole) of diphenyl ether at 80° C. was added to quench the reaction to about 180° C. The solution was filtered at about 180° C. and allowed to cool; the crystals of BPBB began to precipitate at about 140° C. The product was filtered off from diphenyl ether at about 40° C. and was divided into four portions, which were worked up as follows:

I. Washed twice with 350 ml of methanol with agitation, 30 min each wash, followed by filtration. Dried overnight in a vacuum oven at 110° C., the product weighed 35.8 g. Melting peaks a/b (determined as in col. C of Table I), 213/206.

II. Washed twice with 350 ml of tetrahydrofuran with agitation, 30 min each wash, followed by filtration. Dried as above, the product weighed 32.0 g. Melting peaks a/b 215/206.

III. Washed twice with 350 ml of methanol with agitation, 30 min each wash, followed by filtration. Recrystallized from 457 g of 1,2-dichlorobenzene. Washed twice with 350 ml of methanol with agitation, 30 min each wash, followed by filtration. Dried as above, the product weighed 36.7 g. Melting peaks a/b 214/206.

IV. Washed twice with 350 ml of tetrahydrofuran with agitation, 30 min each wash, followed by filtration. Recrystallized from 457 g of 1,2-dichlorobenzene. Washed twice with 350 ml of tetrahydrofuran with agitation, 30 min each wash, followed by filtration. The dry product weighed 26.8 g. Melting peaks a/b 214.206.

Total weight of purified BPBB thus was 131.3 g, for a conversion of 70.8%.

The usefulness of BPBB made in the presence of different catalysts was determined as follows: BPBB was chain extended with 1,3-benzenedicarbonyl chloride and 1,4-benzenedicarbonyl chloride to aromatic poly(ether ketone ketone) in the presence of a capping agent, excess aluminum chloride as catalyst, and 1,2-dichlorobenzene as solvent. After the synthesis, the polymer was filtered off from the solvent, dumped into methanol to decomplex it from aluminum chloride, washed with methanol to extract residual aluminum, and dried. The melt stability was tested with an extrusion plastometer. The following procedure was used in the polymerization experiments.

BPBB, 23.53 g (0.050 mole), 29.32 g (0.22 mole) of aluminum chloride, and 313 g of 1,2-dichlorobenzene were charged to a 1-L magnetically stirred Erlenmeyer flask, which was then stoppered. Separately, 3.54 g (0.017 mole) of 1,4-benzenedicarbonyl chloride, 5.87 g (0.029 mole) of 1,3-benzenedicarbonyl chloride, 0.34 g (0.0024 mole) of benzenecarbonyl chloride, 13.78 g (0.103 mole) of aluminum chloride, and 313 g of 1,2-dichlorobenzene were charged to a 500-ml magnetically stirred Erlenmeyer flask, which was then stoppered. Each mixture was stirred at room temperature for 20 minutes, then cooled down to 0° C. in a water/acetone bath. At 0° C., the contents of the 500-ml flask were transferred to the 1-L flask. The 500-ml flask was washed with 39 g of 1,2-dichlorobenzene, and the wash was transferred to the 1-L flask, which was then stoppered. The combined mixture was held at 0° C. for 30 min and then transferred to a jacketed 1-L resin kettle equipped with a stirrer and a nitrogen purge. The kettle was heated with saturated steam, so that the temperature in the reactor reached 100° C. in about 10 minutes. Solids began to precipitate at about 50° C., indicating the formation of polymer. After one hour at 100° C., the kettle was cooled with running water to 25° C. The slurry was filtered to recover the polymer/aluminum chloride complex produced. The polymer was dumped into a 1-L beaker containing 500 ml of methanol at −15° C., to decomplex the polymer from aluminum chloride. After 30 minutes of agitation, the polymer was filtered off and washed three times for 30 minutes with 500 ml of methanol in a stirred 1-L beaker. The polymer was next washed for 45 minutes with 800 ml of boiling water, filtered, and dried in a vacuum oven for 16 hours at 110° C.

Melt flow rate was determined to evaluate the melt stability of the polymer and also to obtain an indication of its molecular weight. The flow rate was determined according to ASTM D 1238-85 in an extrusion plastometer having a load of 8.2 kg. A flow rate below 10 g/10 minutes indicates that the molecular weight of the polymer is so high that the polymer is hard to process in the melt because of its high viscosity. A flow rate of 10 g/10 minutes represents a number average molecular weight of about 12000. A flow rate above 200 g/10 minutes means that the molecular weight is too low for most applications because of its low modulus of elasticity and tensile strength. At a flow rate of 200 g/10 minutes, the number average molecular weight is about 5000. Normally, the most useful number average molecular weight range for this type of polymers is about 7,000 to 9,000.

The molecular weight was determined by adding 0.025 g of polymer to 25 ml of a mixture of equal weights of phenol and 1,2,4-trichlorobenzene, heating the mixture at 175° C. overnight to dissolve the polymer, filtering the solution at 115° C., and injecting it into a gas chromatograph operating at 115° C. and calibrated with a solution of polystyrene of known molecular weight in the same solvent mixture.

Melt stability was evaluated on the basis of the physical appearance of the extrudate from the plastometer. A smooth extrudate without bubbles means that the polymer is melt stable; a rough and/or bubbly extrudate means that the polymer is not thermally stable.

EXAMPLE 5

The BPBB made in Example 1 in the runs catalyzed by iron (II) chloride tetrahydrate and iron (II) sulfate heptahydrate was recrystallized in each case by dissolving 32 g of BPBB in 457 g of 1,2-dichlorobenzene at 160° C. and filtering hot, cooling the filtrate to 30° C. and recovering BPBB by filtration. BPBB was then washed twice for 30 minutes with 350 ml of methanol, dried in a vacuum oven at 110° C. and ground in a blender. The BPBB was chain extended as described above. The following results were obtained:

TABLE III

| Catalyst | | Flow Rate of Polymer (g/10 min) |
|---|---|---|
| Iron (II) | chloride tetrahydrate | 27 |
| Iron (II) | sulfate heptahydrate | 29 |

The extrudates of both polymers were smooth without bubbles, which is an indication of melt stability. The extrudates of the polymers from BPBB catalyzed by iron (II) chloride tetrahydrate and iron (II) sulfate heptahydrate were, respectively, light brown and dark brown.

COMPARATIVE EXAMPLE 1

A mixture of 53.5 g of diphenyl ether with 0.4 g of anhydrous ferric chloride in a tightly stoppered Erlenmeyer was stirred overnight and then filtered. The ferric chloride retained in the filter was dried and weighed. Based on weight loss, 0.0005 mole (0.078 g) of ferric chloride had dissolved.

One-half of the diphenyl ether/ferric chloride filtrate was combined with 107.3 g of additional diphenyl ether and 20 g (0.099 mole) of 1,4-benzenedicarbonyl chloride in a reactor. The mixture was heated to 250° C. under a nitrogen purge. The color changed from black to red and finally to dark brown, as the reaction proceeded at this temperature for six hours. Diphenyl ether at 80° C., 187 g, was added to the reactor to quench the reaction to about 180° C. The solution was filtered hot and allowed to cool. The product was filtered at 30° C., washed with methanol and dried. It weighed 35.70 g for a conversion of 77.0%. Small amounts of the ortho,-para-isomer were detected by proton nuclear magnetic resonance.

COMPARATIVE EXAMPLE 2

Chain extension was the same as in Example 5, except that the starting BPBB was that of Comparative Example 1. Flow rate in the extrusion plastometer was 104 g/10 min. The extrudate was black and bubbly. This high flow rate and bubbly extrudate indicate that the starting BPBB was not of satisfactory purity and the polymer was not stable in the melt. It is concluded from this Example that unsupported ferric chloride, while catalyzing the formation of BPBB to a high conversion, nevertheless does not produce pure material, suitable for chain extension to a poly(ether ketone ketone).

COMPARATIVE EXAMPLE 3

The BPBB of Example 1 catalyzed by gallium (III) chloride was recrystallized by dissolving 32 g of BPBB in 375 g of N,N-dimethylacetamide at 160° C. and filtering hot, then cooling the filtrate to 30° C. and recovering the BPBB by filtration. The recrystallized material was washed twice for 30 minutes with 350 ml of methanol, dried in a vacuum oven at 110° C., and ground in a blender. This purified BPBB was chain extended as described above, except that the 0.34 g (0.0024 mole) of benzenecarbonyl chloride was replaced by 0.42 g (0.0020 mole) of 3,5-dichlorobenezenecarbonyl chloride. The extrudate from the extrusion plastometer was black, bubbly, and very brittle. Its flow rate was 11 g/10 min. This Example shows that gallium (III) chloride is not a suitable catalyst for making polymerization quality BPBB.

EXAMPLE 6

Same as Example 5, except that the BPBB used was that of Example 1, catalyzed either by gallium (III) sulfate or by indium (III) sulfate hydrate. The results were as follows:

TABLE IV

| Catalyst | Flow Rate of Polymer (g/10 min) |
| --- | --- |
| Gallium (III) sulfate | 21 |
| Indium (III) sulfate hydrate | 20 |

The extrudates of both polymers were quite smooth without bubbles, indicating sufficient melt stability. The color was brown in both cases.

EXAMPLE 7

Each of the four BPBB portions from Example 4 was chain extended as described above. The flow rate and appearance of the respective polymers are given below:

TABLE V

| BPBB Sample | Flow rate (g/10 min) | Physical appearance of extrudate from extrusion plastometer |
| --- | --- | --- |
| I | 35 | dark brown, rough, bubbly |
| II | 44 | dark brown, slightly rough, not bubbly |
| III | 19 | brown, smooth |
| IV | 30 | light brown, smooth |

This example shows that recrystallization of BPBB made with supported ferric chloride gives a material of satisfactory purity for further condensation to a poly(ether ketone ketone).

COMPARATIVE EXAMPLE 4

BPBB was synthesized from diphenyl ether and 1,4-benzenedicarbonyl chloride in 1,2-dichlorobenzene in the presence of excess aluminum chloride, as is known to the art. It was washed several times with methanol and dried. A total of 1.8 kg of dry BPBB was recrystallized by dissolving it in 17 kg of N,N-dimethylacetamide at 160° C., filtering hot, cooling to 30° C., and recovering BPBB by filtration. This material was washed with methanol, dried in a vacuum oven, and ground in a blender. This BPBB was found to be 99.9% pure, as determined by differential scanning calorimetry (first melt and remelt had a peak at 215° C.), ultraviolet/visible spectrophotometry, and proton nuclear magnetic resonance. The BPBB was polymerized by the above-described procedure to a melt-stable material, which had an extrusion plastometer flow rate of 26 g/10 min. The color of the extrudate was amber. This comparative example shows that BPBB polymers made from BPBB prepared in the presence of the catalysts of the present invention give a poly(ether ketone ketone) which, while darker, has about the same molecular weight and melt stability as the poly(ether ketone ketone) made from high purity BPBB prepared in a manner know to the art.

We claim:

1. A process for the manufacture of 1,4-bis(4-phenoxybenzoyl)benzene suitable for chain extension in the presence of aluminum chloride catalyst with a mixture of 1,4-benezenedicarbonyl chloride and 1,3-benzenedicarbonyl chloride, using either benzenecarbonyl chloride or 3,5-dichlorobenzenecarbonyl chloride as the capping agent, to a melt-stable poly(ether ketone ketone), said process comprising contacting diphenyl ether for a period of about 60 to about 360 minutes, at a temperature of about 220°–258° C., with 1,4-benzenedicarbonyl chloride in respective mole ratios of about 5:1 to about 25:1 in the presence of at least one catalyst selected from the group consisting of unsupported iron (II) chloride (ferrous chloride), iron (II) sulfate (ferrous sulfate), gallium (III) sulfate, and indium (III) sulfate; and iron (II) chloride, iron (II) sulfate, gallium (III) sulfate, indium (III) sulfate, and iron (III) chloride (ferric chloride) on an inert support; the mole ratio of 1,4-benzenedicarbonyl chloride to the catalyst being about 10:1 to 1000:1; and recovering the 1,4-bis(4-phenoxybenzoyl)benzene product by separating it from both excess diphenyl ether and the catalyst.

2. A process of claim 1 wherein the reaction temperature is about 240°–258° C.

3. A process of claim 2 wherein the mole ratio of diphenyl ether to 1,4-benzenedicarbonyl chloride is 6–10:1.

4. A process of claim 2 wherein the reaction time is 180–360 minutes.

5. A process of claim 4 wherein the reaction is conducted for about 5 hours at about 250° C.

6. A process of claim 1 wherein the catalyst is an unsupported iron (II) compound.

7. A process of claim 6 wherein the iron (II) compound is ferrous chloride.

8. A process of claim 1 wherein the catalyst is an iron, gallium, or indium compound on an inert support.

9. A process of claim 8 wherein the catalyst is ferric chloride on an inert support.

10. A process of claim 9 wherein the inert support is silica.

* * * * *